US007192764B2

(12) United States Patent
Fukuda et al.

(10) Patent No.: US 7,192,764 B2
(45) Date of Patent: Mar. 20, 2007

(54) CELL SURFACE LAYER-BINDING PROTEIN AND UTILIZATION THEREOF

(75) Inventors: Hideki Fukuda, Kobe (JP); Akihiko Kondo, Kobe (JP); Takeshi Matsumoto, Kobe (JP); Hideo Noda, Amagasaki (JP)

(73) Assignee: Kansai Chemical Engineering, Co., Hyogo (JP)

( * ) Notice: Subject to any disclaimer, the term of this patent is extended or adjusted under 35 U.S.C. 154(b) by 147 days.

(21) Appl. No.: 10/474,431

(22) PCT Filed: Mar. 22, 2002

(86) PCT No.: PCT/JP02/02801

§ 371 (c)(1),
(2), (4) Date: Oct. 9, 2003

(87) PCT Pub. No.: WO02/085935

PCT Pub. Date: Oct. 31, 2002

(65) Prior Publication Data

US 2004/0197857 A1 Oct. 7, 2004

(30) Foreign Application Priority Data

Apr. 19, 2001 (JP) ............................. 2001-121233

(51) Int. Cl.
| | |
|---|---|
| C12N 1/19 | (2006.01) |
| C12N 9/00 | (2006.01) |
| C12N 15/00 | (2006.01) |
| C07K 14/39 | (2006.01) |
| C07H 21/04 | (2006.01) |

(52) U.S. Cl. ................ 435/254.2; 435/183; 435/320.1; 530/350; 536/23.74

(58) Field of Classification Search ..................... None
See application file for complete search history.

(56) References Cited

U.S. PATENT DOCUMENTS 6,027,910 A * 2/2000 Klis et al. ..................... 435/41

FOREIGN PATENT DOCUMENTS

| JP | 11-290078 | 10/1999 |
|---|---|---|
| JP | 11-290078 A | 10/1999 |
| JP | 8-506484 | 5/2001 |
| WO | WO 94/18330 A1 | 8/1994 |
| WO | WO 00/66755 | 11/2000 |

OTHER PUBLICATIONS

Murai, et al., "Construction of a Starch-Utilizing Yeast by Cell Surface Engineering," *Applied and Environmental Microbiology*, Apr. 1997, pp. 1362-1366.
Watari, et al., "Breeding of Flocculent Industrial *Saccharomyces cerevisiae* Strains by Introducing the Flocculation Gene FLOI," *Agric. Biol. Chem.*, 55 (6), 1991, pp. 1547-1552.
Stewart, et al., "The Identification, Characterization, and Mapping of a Gene for Flocculation in *Saccharomyces* sp.," *Can. J. Microbiol*, vol. 23, 1977, pp. 441-447.
Russell, et al., "Revised Nomenclature of Genes that Control Yeast Flocculation," *J. Inst. Brew.*, May-Jun. 1980., vol. 86, pp. 120-121.
Lewis, et al., "The Genetics of Yeast Flocculation," *J. Inst. Brew.*, May-Jun. 1976, vol. 82, pp. 158-160.
Russell, et al., "Spheroplast Fusion of Brewer's Yeast Strains," *J. Inst. Brew.*, Mar.-Apr., 1979, vol. 85, pp. 95-98.
Yamashita, et al., "Isolation of Glucoamylase-non-producing Mutants in the Yeast *Saccharomyces diastaticus*," *Agric. Biol. Chem.*, 48 (1), 1984, pp. 131-135.
Beer, et al., "Cloning, Expression, Characterization and Role of the Leader Sequence of a Lipase from *Rhizopus oryzae*," *Biochimica et Biophysics Acta* 1399 (1998), pp. 173-180.
Kaieda, et al., "Biodiesel Fuel Production from Plant Oil Catalyzed by *Rhizopus oryzae* Lipase in a Water-Contaning System without an Organic Solvent," *Journal of Bioscience and Bioengineering*, vol. 88, No. 6, 1999, pp. 627-631.
Smit, et al., "Flocculence of *Saccharomyces cerevisiae* Cells Is Induced by Nutrient Limitation, with Cell Surface Hydrophobizity as a Major Determinant," *Applied and Environmental Microbiology*, Nov. 1992, pp. 3709-3714.
Kondo, et. al., "Development of Cell Display Systems and Their Utilization," *Applied and Environmental Microbiology*, vol. 5, No. 2, 2001, pp. 121-126. (Partial Translation).
Lipke, et al, "AGal is the Structural Gene for the *Saccharomyces cerevisiae* α-Agglutinin, a Cell-Surface Glycoprotein Involved in Cell-Cell Interactions during Mating," *Molecular & Cellular Biology*, Aug. 1989. p. 3155-3165, American Society for Microbiology.
Bony, et al, "Localization and Cell Surface Anchoring of the *Saccharomyces cerevisiae* Flocculation Protein Flo1p," *Journal of Bacteriology*, Aug. 1997, p. 4929-4936, American Society for Microbiology.
Schreuder, et al, "Immobilizing proteins on the surface of yeast cells," *TIBTECH*, Apr. 1996, vol. 14, Elsevier Science Ltd.
Matsumoto, et al., "Construction of Yeast Strains with High Cell Surface Lipase Activity by Using Novel Display Systems Based on the Flo1p Flocculation Functional Domain," *Applied & Environmental Microbiology*, Sep. 2002, vol. 68, No. 9, p. 417-4522. American Society for Microbiology.
Kondo, et al., "Yeast cell-surface display—applications of molecular display," *Appl. Microbiol. Biotechnical*, 2004, 64: p. 28-40, published online: Jan. 10, 2004, Spring-Verlag 2004.
Supplementary European Search Report, Sep. 29, 2004.
Kondo, et al., "Yeast Cell Surface Display Applications of Molecular Display," *Gene and Medicine*, (2004) 64: 28-40.
Steen, et al., "AcmA of *Lactoccur lactis* is an N-acetylglucosaminidase with an optimal number of LysM domains for proper functioning," *FEBS Journal* 272 (2005) 2854-2868.
Steen, et al., "Cell Wall Attachment of a Widely Distributed Peptidoglycan Binding Domain Is Hindered by Cell Wall Constituents," *The Journal of Biological Chemistry*, vol. 278, No. 26, Issue of Jun. 27, p. 23874-23881, 2003, USA.
Raha, et al., "Cell Surface Display System for *Lactococcus lactis*: A Novel Development for Oral Vaccine," *Applied Genetics and Molecular Biotechnology*, (2005) 68: 75-81.

* cited by examiner

*Primary Examiner*—Robert A. Wax
(74) *Attorney, Agent, or Firm*—Jagtiani + Guttag (57) ABSTRACT

A plasmid is constructed so as to express a fused protein of a sugar chain-binding protein domain with a desired protein. Then this plasmid is transferred into cells and thus the protein is expressed in the cell surface layer. This method is particularly adequate in case of expressing a protein having an activity in the C-terminal portion in cell surface layer.

15 Claims, 3 Drawing Sheets

Activity    Growth
◆ Δkex2-long    ◇
★ Δkex2-short   △
● YF207-long    ○
▼ YF207-short   ▽
■ MT8-1-long    □
★ MT8-1-short   ☆

Fig. 3

CELL SURFACE LAYER-BINDING PROTEIN AND UTILIZATION THEREOF

CROSS-REFERENCE TO RELATED APPLICATIONS

This application is a national stage application of PCT/JP02/02801, entitled "Cell surface layer-binding protein and utilization thereof," filed on Mar. 22, 2002, which claims the priority of Japanese Patent Application No. 2001-12 1233, entitled "Cell surface layer-binding protein and utilization thereof," filed on Apr. 19, 2001. The entire contents and disclosure of which are hereby incorporated by reference.

TECHNICAL FIELD

The present invention relates to a cell surface layer-binding protein having a sugar chain-binding protein domain, in which an additional protein is bound at least to the N-terminus or the C-terminus of the sugar chain-binding protein domain.

BACKGROUND ART

Cell surface layer-localized proteins are proteins that are present and immobilized in a cell surface layer. An example thereof is α- or a-agglutinin, which is a flocculation protein of yeast. Such proteins are similar to secretory proteins in that they have secretion signal sequences, but are different from secretory proteins in that they are transported while being immobilized in a cell membrane via a GPI anchor. In general, cell surface layer-localized proteins have a GPI anchoring domain on the C-terminal portion. Cell surface layer-localized proteins are immobilized on a cell membrane in the following manner: when the protein to be localized on the cell surface layer is passing across a cell membrane, a part (i.e., a GPI anchor attachment recognition signal sequence) of the domain of the protein is selectively cleaved, a newly projected C-terminal portion of the protein is bound to the GPI anchor on the cell membrane, and thus the protein is immobilized on the cell membrane. Then, the base portion of the GPI anchor is cleaved by phosphatidylinositol-dependent phospholipase C (PI-PLC). Then, the protein cleaved from the cell membrane is incorporated into the cell wall so as to be immobilized on the cell surface layer and thus is localized on the cell surface layer. Herein, "GPI anchor" refers to a glycolipid having ethanolamine phosphate–6 mannose α 1-2 mannose α 1-6 mannose α 14 glucosamine α 1-6 inositol phospholipid, which is also known as glycosylphosphatidylinositol (GPI), as the basic structure.

The GPI anchoring domain is generally positioned at or near the C-terminus of the cell surface layer-localized protein. For example, in addition to the GPI anchor attachment recognition signal sequence, there are four sugar chain-binding sites in the sequence encoding 320 amino acid residues from the C-terminus of α-agglutinin. These sugar chain-binding sites and polysaccharides constituting the cell wall are covalently bonded after the GPI anchor is cleaved by PI-PLC, so that the C-terminal sequence portion of α-agglutinin is bonded to the cell wall and thus the α-agglutinin is retained on the cell surface layer.

The inventors succeeded in expressing lipase on the cell surface layer, utilizing such a GPI anchoring domain (Japanese Laid-Open Patent Publication No. 11-290078). More specifically, the structural gene of lipase was placed upstream of the DNA encoding the GPI anchoring domain, and a secretion signal sequence was placed further upstream, so that the lipase was expressed on the cell surface layer such that the N-terminus thereof was outside the cell.

DISCLOSURE OF INVENTION

The thus expressed protein can exhibit sufficient activity in the cell surface layer, as long as it has the active center on the N-terminal portion. However, when the active center is on the C-terminal portion, the active center is too dose to the cell surface layer so that steric hindrance may occur and prevent sufficient activities from being exhibited.

The inventors have examined various methods for expressing a protein on the cell surface layer. As a result, it was unexpectedly found that even if the function of the GPI anchoring domain, which had been considered to be essential, was lost, the GPI anchor protein could be retained on the cell surface layer, and thus the present invention was achieved. In other words, the present invention has made it possible that if at least the flocculation functional domain of the GPI anchor protein is contained, a desired protein can be expressed on a cell surface layer by constructing a plasmid that allows the desired protein to be expressed on either the N-terminus or the C-terminus or both the N-terminus and the C-terminus.

The present invention provides a cell surface layer-binding protein comprising a sugar chain-binding protein domain, in which an additional protein is fused to at least an N-terminus or a C-terminus of the sugar chain-binding protein domain.

In a preferable embodiment, the sugar chain-binding protein domain is a portion including at least a flocculation functional domain of a GPI anchor protein.

In a preferable embodiment, the GPI anchor protein is a flocculation protein.

In a preferable embodiment, the flocculation protein is a protein selected from the group consisting of FLO1, FLO2, FLO4, FLO5, FLO9, FLO10 and FLO11.

In another preferable embodiment, the additional protein is fused to the N-terminus of the sugar chain-binding protein domain.

In a more preferable embodiment, the additional protein is fused to the C-terminus of the sugar chain-binding protein domain.

In a preferable embodiment, the additional protein is lipase.

In a preferable embodiment, the additional protein is an antibody.

In a preferable embodiment, the same or different additional proteins are fused to the N-terminus and the C-terminus of the sugar chain-binding protein domain.

The present invention also provides DNA encoding the above-described cell surface layer-binding protein.

The present invention further provides a plasmid comprising the above-described DNA.

The present invention further provides a cell wherein the DNA or the plasmid is introduced, and the additional protein is expressed on a cell surface layer.

In a preferable embodiment, the cell is yeast.

In a preferable embodiment, the additional protein is an enzyme.

The present invention also provides a method for using the above-described cell wherein the additional protein is contacted with a substrate, so that the substrate is bound or the substrate is converted into another substance.

The present invention also provides an enzyme-containing agent comprising the above-described cell.

BEST MODE FOR CARRYING OUT THE INVENTION

In the present invention, "cell surface layer-binding protein" refers to a fused protein that includes at least a sugar chain-binding protein domain and another protein and is immobilized on a cell surface layer by the sugar chain-binding protein domain.

In the present invention, "sugar chain-binding protein domain" refers to a domain that has a plurality of sugar chains and can stay on a cell surface later due to interaction and/or entwinement between these sugar chains and the sugar chains in the cell wall. Examples thereof include sugar chain-binding sites of lectin, lectin-like protein and the likes. A typical example thereof is a flocculation functional domain of the GPI anchor protein. Here, "flocculation functional domain of the GPI anchor protein" refers to a domain that is positioned on the N-terminal portion of the GPI anchoring domain, has a plurality of sugar chains, and is considered to participate in flocculation.

In the present invention, "GPI anchor protein" generally refers to a cell surface layer localized protein that can be bound to a cell membrane via the GPI anchor present on the cell membrane. The GPI anchor protein has a secretion signal sequence at the N-terminus and the GPI anchoring domain at the C-terminus. Examples of the GPI anchor protein include, but are not limited to, a flocculation protein of yeast (α-agglutinin, a-agglutinin, and FLO proteins), and alkaline phosphatase. In particular, FLO proteins, such as FLO1, FLO2, FLO4, FLO5, FLO9, FLO10 and FLO11 can be preferably used as the flocculation protein in the present invention.

In the present invention, "GPI anchoring domain" refers to a domain constituting from a cell wall anchoring domain and a GPI anchor attachment recognition signal sequence. In general, the GPI anchoring domain is positioned at or near the C-terminus of a cell surface layer-localized protein. For example, in an α-agglutinin of yeast, the GPI anchoring domain is a sequence of 320 amino acids from the C-terminus.

The GPI anchor attachment recognition signal sequence of the GPI anchoring domain is a portion that recognizes the GPI anchor on a cell membrane. After the GPI anchor attachment recognition signal sequence at the C-terminus is cleaved, the GPI anchor is bound to a newly projected C-terminus. Then, the base portion of the bound GPI anchor is cleaved by PI-PLC, and thus the protein is detached from the cell membrane and incorporated into the cell wall. Here, the sugar chains present in the cell wall anchoring domain are bound to the sugar chains in the cell wall and thus the protein is immobilized on the cell surface layer.

The cell surface layer-binding protein of the present invention includes (1) a fused protein in which an additional protein is fused to the N-terminus of the sugar chain-binding protein domain, (2) a fused protein in which an additional protein is fused to the C-terminus of the sugar chain-binding protein domain, and (3) a fused protein in which the same or different proteins are fused both to the N-terminus and the C-terminus of the sugar chain-binding protein domain. The additional protein may be fused directly to the sugar chain-binding protein domain or may be fused thereto via a linker. The secretion signal sequence is fused to the N-terminus of the N-terminus-bound additional protein.

There is no limitation regarding the additional protein that constitutes the cell surface layer-binding protein of the present invention, but a protein that is not originally localized on the cell surface layer and is placed for the purpose of immobilization on the cell surface layer is preferable. Examples thereof include secretory proteins and antibodies. Examples of secretory proteins include lipase, amylases (glucoamylase, α-amylase and the like), cellulases, fluorescent protein, protein A and derivatives thereof.

It can be determined whether these enzymes are fused on the N-terminus or the C-terminus, depending on their characteristics. In particular, a protein having the active center on the C-terminal region such as lipase is preferably fused to the C-terminus of the sugar chain-binding protein domain. This protein may be directly fused to the C-terminus of the sugar chain-binding protein domain, or may be fused, for example, via a part of the GPI anchoring domain.

It is preferable that the protein is fused between the secretion signal sequence and the sugar chain-binding protein domain when it is fused to the N-terminus. Furthermore, for example, a part of the GPI anchoring domain may be contained on the C-terminus of the sugar chain-binding protein domain. However, in this case, the GPI anchor attachment recognition signal is not contained, and therefore it is not via the GPI anchor that an expressed fused protein is immobilized on the cell surface layer.

The secretion signal sequence is an amino acid sequence that is bound to the N-terminus of a protein (secretory protein) that is secreted outside a cell (including periplasm) and contains a large number of hydrophobic amino acids. In general, the secretion signal sequence is removed when the secretory protein passes across a cell membrane from the inside of a cell and is secreted outside the cell.

In the present invention, any secretion signal sequence can be used, as long as it can lead an expressed fused protein to the cell membrane, and there is no limitation regarding its origin. For example, as the secretion signal sequence, the secretion signal sequence of glucoamylase, the signal sequence of α- or a-agglutinin of yeast, the secretion signal sequence of lipase can be preferably used. A part of or the entire secretion signal sequence and/or the prosequence thereof can remain in the N-terminus, as long as it does not affect the activity of the additional protein fused with the cell surface layer-binding protein.

In this specification, "lipase" refers to a protein (enzyme) having an activity that can allow a fatty acid to be released from oils and fats. Herein, "oils and fats" refers to glycerol bound to a fatty acid. There is no particular limitation regarding the origin of the lipase, as long as it has such an activity. In general, lipase derived from microorganisms, plants, and animals (e.g., porcine pancreas) can be used. Furthermore, lipase can be 1,3-specific or can be nonspecific. For example, biodiesel fuel can be produced from waste oil by expressing lipase on the cell surface layer of flocculent yeast.

In this specification, "amylases" refer to enzymes that hydrolyze starch. Typical examples thereof include glucoamylase and α-amylase, and further include β-amylase and isoamylase.

In this specification, "glucoamylase" refers to an exo-type hydrolase that cleaves glucose units from the non-reducing end of starch. There is no particular limitation regarding its origin, as long as it has such an activity. In general, glucoamylase derived from fungi such as Rhizopus and Aspergillus can be used. For example, as described in Ueda et al. (Appl. Environ. Microbiol. 63:1362–1366 (1997)), glucoamylase derived from Rhizopus oryzae can be preferably used. For example, ethanol can be produced efficiently in the presence of starch by expressing glucoamylase on the surface layer of yeast.

In the present invention, "α-amylase" refers to an endo-type enzyme that hydrolyses only α1,4-glucoside bond of starch. There is no particular Imitation regarding its origin, as long as it has such an activity. For example, α-amylase derived from animals (saliva, pancreas, etc.), plants (malt, etc) and microorganisms are used. For example, ethanol can be produced efficiently in the presence of starch by expressing α-amylase on a yeast surface layer. Alcoholic fermentation can be performed efficiently when α-amylase is expressed in combination with the glucoamylase.

"Cellulases" generally refers to endo β1,4-glucanase, but in the present invention, cellulase refers to a group of enzymes that is produced together with β1,4-glucanase, cleave a β1,4-glucoside bond and produce glucose from cellulose (e.g., cellobiohydrolase, β-glucosidase). Examples of cellulases include endo β1,4-glucanase, cellobiohydrolase, β-glucosidase, and carboxymethyl cellulase. There is no particular limitation regarding its origin, as long as it has such an activity. For example, cellulases derived from microorganisms can be preferably used.

Alcoholic fermentation can be performed efficiently from a woody material such as paper, pulp or their waste materials by expressing cellulase alone or in combination on a yeast surface layer.

In the present invention, there is no particular limitation regarding cells in which a protein is expressed on its cell surface layer, as long as they have a cell wall such as bacteria, fungi, or plant cells. Preferably, yeast can be used.

The cell used in the present invention is a cell that has been transformed by introducing DNA such that a desired protein is displayed on the cell surface layer. The DNA to be introduced includes sequences encoding at least the secretion signal sequence, the sugar chain-binding protein domain and a desired protein. Furthermore, the DNA may include a sequence encoding another desired protein.

The synthesis and ligating of the DNA containing the various sequences can be performed by techniques that can be used generally by those skilled in the art.

It is desirable that the DNA is in the form of a plasmid. It is preferable that the DNA is a shuttle vector for *E. coli* in that the DNA can be amplified and obtained easily. The starting material of the DNA has, for example, a replication origin (Ori) of a 2 μm plasmid of yeast and a replication origin of ColE1 and more preferably, it further has a yeast selective marker (e.g., a drug resistant gene, TRP, LEU2, etc.) and an *E. coli* selective maker (drug resistant gene, etc.). In order to express a structural gene of a protein, it is desirable that the DNA starting material contains a so-called regulatory sequence for regulating the expression of this gene, such as operators, promoters, terminators and enhancers. Examples thereof include a GAPDH (glyceraldehyde 3'-phosphate dehydrogenase) promoter and a GAPDH terminator. Examples of a plasmid of such a starting material include plasmid pYGA2270 or pYE22m containing a GAPDH (glyceraldehyde 3'-phosphate dehydrogenase) promoter sequence and a GAPDH terminator sequence, or a plasmid pWI3 containing UPR-ICL (an upstream region of isocitrate lyase) sequence and Term-ICL (a terminator region of isocitrate lyase) sequence.

Preferably, if DNA encoding a desired protein is inserted between the GAPDH promoter sequence and the GAPDH terminator sequence of the plasmid pYGA2270 or pYE22m, or between the UPR-ICL sequence and the Term-ICL sequence of the plasmid pWI3, a plasmid for yeast transformation can be constructed. In the present invention, a multicopy plasmid pWIFS or pWIFL is used preferably, and for example, pWIFSpmROL or pWIFLpmROL is produced.

As the yeast serving as a host, any yeast can be used, but flocculent yeast is preferable in that it is easily separated after a reaction, or in that it is easily immobilized so that sequential reactions can be performed. Alternatively, when a flocculation functional domain is used as the sugar chain-binding protein domain, strong flocculation properties can be provided to any yeast.

Examples of flocculent yeast include *Saccharomyces diastaticus* ATCC60715, *Saccharomyces diastaticus* ATCC60712, *Saccharomyces cerevisiae* IF01953, *Saccharomyces cerevisiae* CG1945, and *Saccharomyces cerevisiae* HF7C. Alternatively, new flocculent yeast can be constructed. For example, as shown in Example 1 described later, according to the method of M. D. Rose et al. (Methods in Yeast Genetics, 1990, Cold Spring Harbor Laboratory Press, Cold Spring Harbor, N.Y.), flocculent yeast YF207 and yeast having properties equal to those of this yeast can be obtained from diploid by conjugation of flocculent yeast ATCC60712 and non-flocculent yeast W303-1B. The flocculent yeast YF207 strain obtained by the inventors of the present invention has excellent plasmid stability, and a very high fermentative ability. Therefore, when a recombinant flocculent yeast YF207 strain is used in which either α-amylase or glucoamylase alone or both α-amylase and glucoamylase are expressed on the cell surface layer, the efficiency of alcoholic fermentation from starch is very high.

The cells used in the method of the present invention can be obtained by introducing the above-described DNA into cells. "Introduction of DNA" means that DNA is introduced into a cell and expressed therein. Example of the method for introducing DNA include transformation, transduction, transfection, cotransfection, and electroporation, and specific examples thereof include a method employing lithium acetate and a protoplast method.

The DNA to be introduced may be in the form of a plasmid as described above, or may be incorporated into a chromosome by inserting DNA into a gene of a host or causing homologous recombination between DNA and a gene of a host.

The cell into which the DNA is introduced can be selected by a selective marker (e.g., TRP) and selected by measuring the activity of the expressed protein. The fact that the protein is immobilized on the cell surface layer can be confirmed by an immunological method employing anti-protein antibody and FITC labeled anti-IgG antibody.

The cells used in the present invention can be immobilized on a carrier. For example, in the case of yeast, immobilization thereon is convenient when it is used in repeated batch fermentation or continuous fermentation.

In this specification, "carrier" means a substance on which a cell can be immobilized, and preferably a substance that is insoluble in water or a specific solvent. As a material of the carrier that can be used in the present invention, foams or resins, for example, polyvinyl alcohol, polyurethane foam, polystyrene foam, polyacrylamide, a polyvinyl formal resin porous substance, silicon foam, or a cellulose porous substance are preferable. In view of exfoliation of cells whose growth and activities are reduced or dead cells, porous carriers are preferable. The size of openings of pores of the porous substance depends on the cell, but a suitable size of the openings is such that the cells can enter sufficiently within the pores and be grown therein. A size of 50 μm to 1000 μm is preferable but the size is not limited thereto.

The carrier may be of any shape. In view of the strength of the carrier, cultivation efficiency and the like, a spherical or cubical shape is preferable. Preferable size is 2 mm to 50 mm in a diameter for a spherical carrier preferable and 2 mm to 50 mm in length of the side for a cubical carrier.

In this specification, "immobilization of a cell" means a state in which a cell is not free, for example, a state in which a cell is bound or attached on a carrier, or incorporated into the inside of the carrier. For immobilization of a cell, methods commonly used by those skilled in the art, such as a carrier binding method, a cross-linking method, or an entrapment method, can be used. Among these, for immobilization of flocculent yeast, a carrier binding method is most suitable. The carrier binding method includes a chemically adsorption method by which the cells are adsorbed to ion-exchange resin or a physically adsorption method.

For example, although the flocculent yeast that can be used in the present invention is immobilized on a carrier, it can grow thereon and has the properties that the yeast is exfoliated spontaneously with the reduction in its activity. Therefore, the yeast bound to the carrier is characterized by maintaining a substantially constant number of live yeast and having high activities. In view of these characteristics, physical adsorption is most preferable for binding to the carrier. No special means is required for physical adsorption. Flocculent or adhesive cells are simply mixed with the porous carrier and cultivated so that the cells enter the pores of the porous carrier and are adhered to the carrier.

In this specification, "flocculation properties" means the property that cells such as yeast that are floating or dispersed in a liquid aggregate and form a mass (flocculate), and "adhesiveness" means the properties that cells are adhered or bound to each other so as to form an aggregate.

In this specification, a "state in which the activity is reduced" means a state in which the activity of an entire cell is weakened although the cell itself is not dead, or for example, a state in which the activity involved in flocculation is reduced or the activity in the DNA level encoding an enzyme involved in flocculation is weakened so that cells cannot aggregate.

In the present invention, flocculent or adhesive yeast may be yeast that is provided with the flocculation properties or adhesiveness by introduction of a gene involved in flocculation or adhesion.

Examples of genes involved in flocculation or adhesion include substances involved in flocculation or adhesion, such as structural genes encoding chitin, lectin, etc. in yeast. Examples of genes involved in the flocculation include genes such as FLO1 [J. Watari et al., Agric. Biol. Chem., 55:1547(1991), G. G. Stewart et al., Can. J. Microbiol., 23:441(1977), I. Russell et al., J. Inst. Brew., 86:120(1980), C. W. Lewis et al. J. Inst. Brew., 82:158(1976)], FLO5 [I. Russell et al., J. Inst. Brew., 85:95(1979)], and FLO8 [I. Yamashita et al., Agric. Biol. Chem., 48:131(1984)].

These genes involved in flocculation or adhesion are incorporated in the plasmid of the above-described starting material and are introduced in a cell together with DNA that is designed such that a desired protein is displayed on the cell surface layer.

The thus obtained immobilized cell can be cultivated in a floated state while being attached onto a carrier or can be filled in a column or the like and used as a so-called bioreactor. Even if the cells are repeatedly cultivated and reacted continuously or by batch, cells whose activities are reduced or that are dead are exfoliated so that the activity of the cells is not reduced, and the cells can be utilized efficiently.

The cells of the present invention obtained in the above-described manner can be used for the purpose of binding a substrate or converting a substrate to another substance by contacting the protein expressed on the cell surface layer with the substrate. For example, when the protein is an enzyme, the cell can be provided as an enzyme-containing agent that includes a cell expressing that enzyme. More specifically, the enzyme-containing agent of the present invention includes a suspension containing the cells of the present invention and a medium that can maintain the cells, and those obtained by cryopreservation, lyophilization or low-temperature drying of the cells of the present invention.

Furthermore, the cells of the present invention can also be used as a combinatorial library by allowing each of various proteins to which a mutation is introduced at random to be displayed on the surface layer of another cell. It is possible to select a clone having most suitable properties for the purpose rapidly and easily. The "combinatorial library" in this specification refers to a group of various mutants in which a mutation is introduced randomly at the gene level so that the variety of the protein is expanded artificially.

Hereinafter, the present invention will be described by way of example, but is not limited thereto.

Example 1

Preparation of DNA Having the 5' Region of FLO1 and the Structural Gene of Prolipase in this Order A: Preparation of a Gene of the 5' Region (Signal Sequence and Flocculation Functional Domain) of FLO1

A gene of FLO1 was obtained in the following manner. First, a chromosomal DNA was extracted from *S. cerevisiae* ATCC60715. Then, using this as a template, PCR amplification was performed using nucleotide sequences described in SEQ ID NOS: 1 and 2 as primers, and the amplified product was digested with BamHI and BglII to give a BamHI-BglII fragment (3300 bp BamHI-BglII FLO1 fragment) having a length of about 3300 bp. This 3300 bp fragment seems to have a sequence of the 5' region of the FLO1 (secretion signal sequence and a FLO1 flocculation functional domain).

B: Preparation of a Lipase Gene

A gene of *Rhizopus oryzae* lipase was prepared in the following manner. Briefly, first, a chromosomal DNA was extracted from *R. oryzae* IFO4697. Then, using this as a template, PCR amplification was performed using the nucleotide sequences described in SEQ ID NOS: 3 and 4 as primers, and the amplified product was digested with BamHI and SalI to give a BamHI-SalI fragment (BamHI-SalI lipase fragment) having a length of about 1100 bp. This lipase fragment had the pro-sequence and the mature protein sequence of lipase and is substantially the same sequence as those described in the report of Beer et al. (Biochim Biophys Acta, 1399: 173–180, 1998).

Figure 1:
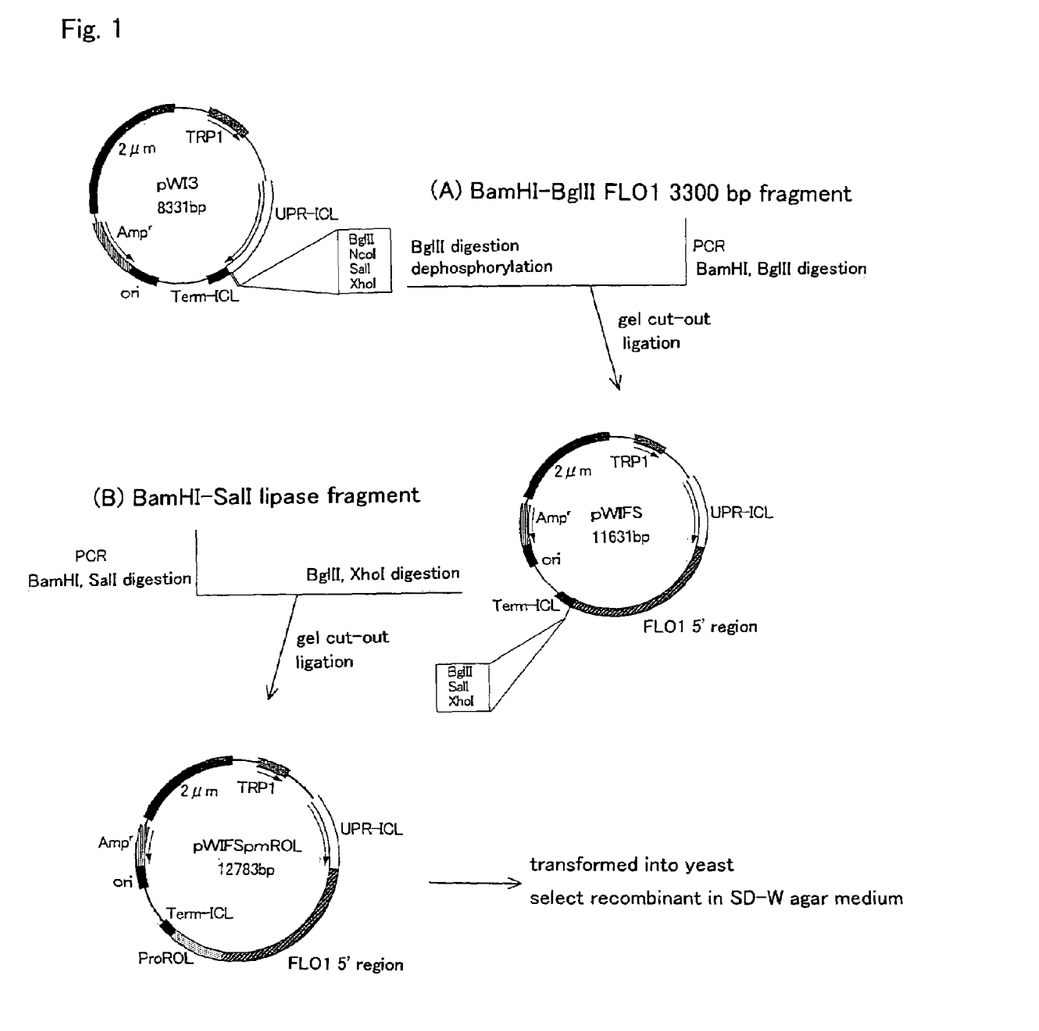
FIG. 1 is a schematic view of construction of a plasmid pWIFSpmROL.

C: Construction of a Plasmid Having the 5' Region of FLO1 and the Structural Gene of Prolipase in this Order A plasmid having a desired DNA can be obtained by connecting the 5' region gene of FLO1 obtained in the above section A and the prolipase gene obtained in the above section B. In order to prepare a fused protein of a FLO1 derivative and lipase, the following procedure was performed. A schematic view of the preparation is shown in FIG. 1.

First, a multicopy plasmid pWI3 was digested with BamHI and dephosphorized, and then the 3300 bp BamHI-BglII FLO1 fragment obtained in the above section A was inserted therein to give plasmid pWIFS. Then, this plasmid pWIFS was digested with BglII and XhoI, and the BamHI-SalI lipase fragment obtained in above section B was inserted therein to give pWIFSpmROL. The protein expressed from the gene that is inserted in this plasmid pWIFSpmROL was designated "short-type FLO1-lipase".

Example 2

Preparation of DNA Having the 5' Region of FLO1 Including a Cell Wall Anchoring Domain and the Structual Gene of Prolipase in this Order A chromosomal DNA of FLO1 was extracted in the same manner as in Example 1. Using this as a template, PCR amplification was performed using the nucleotide sequences described in SEQ ID NOS: 1 and 5 as primers, and the amplified product was digested with BamHI and BglII to give a BamHI-BglII fragment (4500 bp BamHI-BglII FLO1 fragment) having a length of about 4500 bp. This 4500 bp fragment seems to have a sequence of the 5' region of the FLO1 (secretion signal sequence and a FLO1 flocculation functional domain).

The same operation as in Example 1 was performed using the obtained 4500 bp BamHI-BglII FLO1 fragment. More specifically, the 4500 bp fragment, instead of the 3300 bp BamHI-BglII FLO1 fragment of Example 1 was inserted in pWI3 to give a plasmid pWIFL. Then, the BamHI-SalI lipase fragment was inserted in this plasmid pWIFL in the same manner as in Example 1 to give pWIFLpmROL. The protein expressed from the gene that was inserted in this plasmid pWIFLpmROL was designated "long-type FLO1-lipase"

Example 3

Preparation of Yeast Having Lipase on a Cell Surface Layer

Using *Saccharomyces diastaticus* ATCC60712 (MATα leu2-4 3,112 his2 lys2 sta1 FL08), which is a flocculent yeast, and W303-1B (MATα ura3-52 trp1 Δ2 leu2-3,112 his3-11 ade2-1 can1-100), which is a non-flocculent yeast, according to the method of M. D. Rose et al. (described above), *Saccharomyces cerevisiae* YF207 (MATα ura3-52 trp1 Δ2 his ade2-1 can1-100 sta1 FLO8), which is a new flocculent strain that is tryptophan auxotrophic, was obtained.

Figure 2:
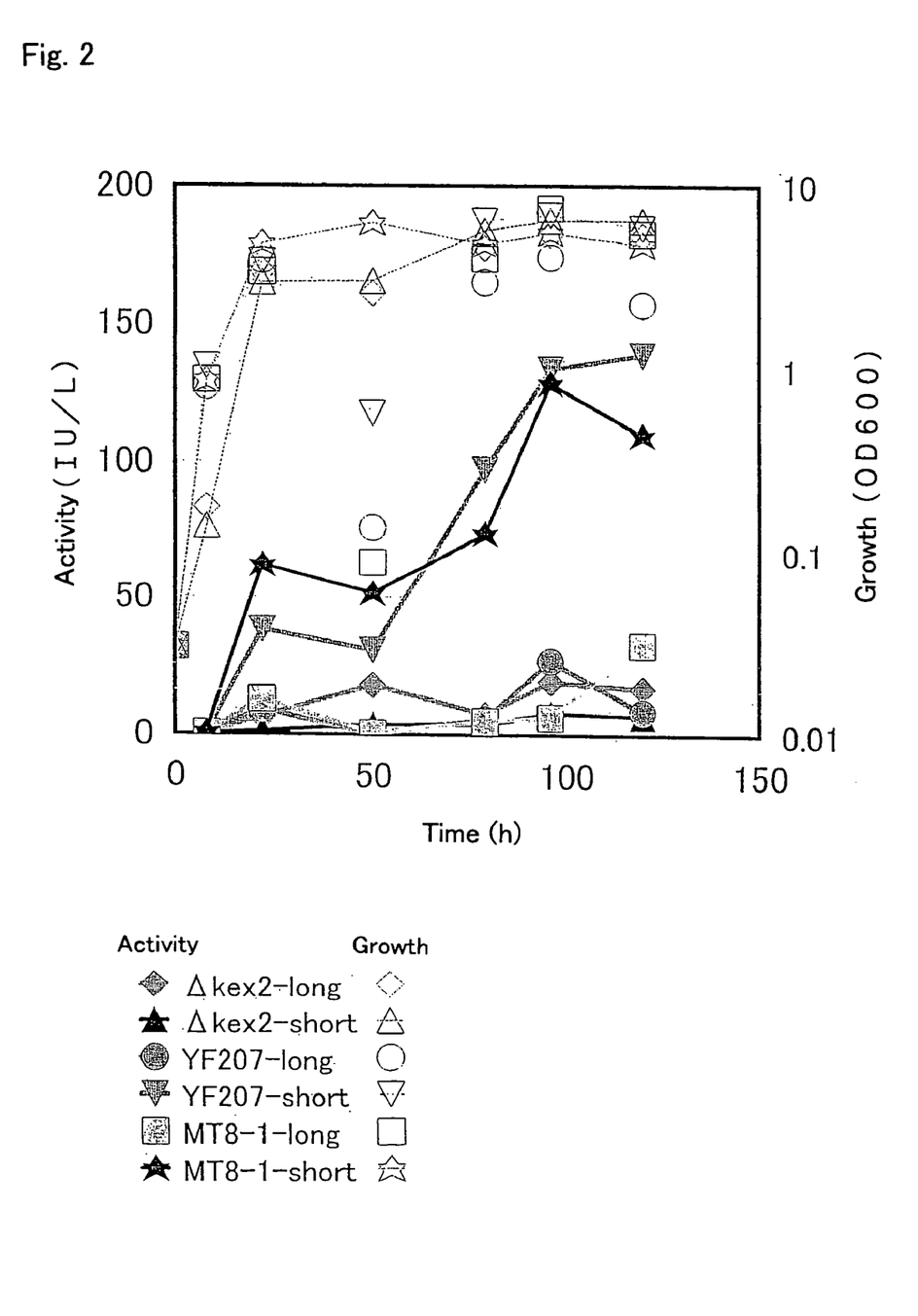
FIG. 2 is a graph showing the growth of various yeasts having lipase on a cell surface layer and the lipase activities in the yeasts.

The plasmid pWIFSpmROL obtained in Example 1 and the plasmid pWIFLpmROL obtained in Example 2 were introduced in non-flocculent yeast *S. cerevisiae* MT8-1 (MATA ade his3 leu2 trp1 ura3) (Tajima et al., Yeast, 1:67-77, 1985) or flocculent yeast YF207 by a lithium acetate method employing Yeast Maker (Clontech Laboratories, Inc., Palo Alto, Calif.). They were cultivated using a SD-W agar selective medium (6.7% Yeast nitrogen base w/o amino acids (manufactured by Difco Laboratories), 2% glucose and 2% agar powder) supplemented with L-tryptophan-free suitable amino acids and bases. The grown yeast was selected, and yeast expressing the short-type FLO1-lipase was designated "MT8-1-short" and "YF207-short", respectively, and yeast expressing the long-type FLO1-lipase was designated "MT8-1-long" and "YF207-long", respectively The obtained yeast was cultivated in a SDC liquid medium, and separated into a medium and cells by centrifugation and each lipase activity was measured. As the controls, yeast in which the plasmid pWI3 was introduced into *S. cerevisiae* MT8-1 was used. As a result, in the controls, the lipase activity was not observed in either the medium or the cells. Although the lipase activity was substantially not observed in the culture supernatants of the transformants MT8-1-short, YF207-short, MT8-1-long, and YF207-long, the yeast cells themselves of all the types had the lipase activities (FIG. 2). The lipase activities were measured using a Lipase Kit S (manufactured by DAINIPPON PHARMACEUTICAL CO., LTD.).

Example 4

Confirmation of the Function of Yeast Having Lipase on the Cell Surface Layer

Regarding the yeast MT8-1-short and YF207-short which express the short-type FLO1-lipase, and the yeast MT8-1-long and YF207-long which express the long-type FLO1-lipase, obtained in Example 3, the growth of the cell of each type was measured based on the absorbance at a wavelength of 600 nm. It was found that all of the types of yeast were grown well in a medium to the same extent as that of the controls (data not shown).

Figure 3:
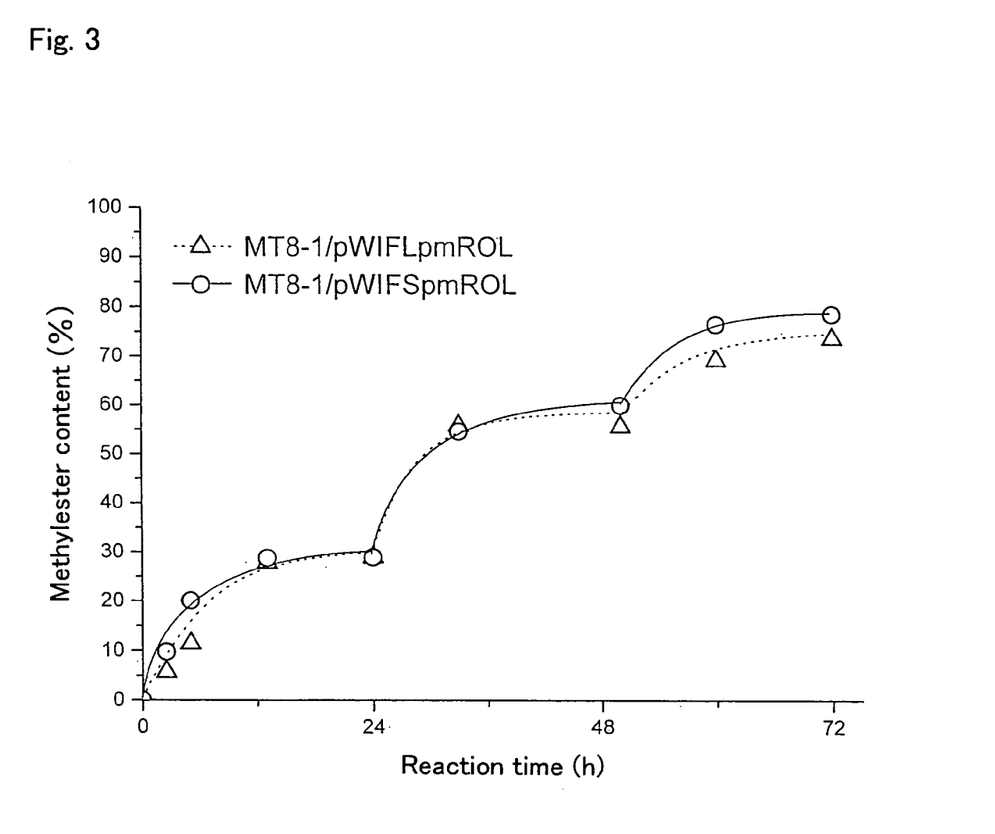
FIG. 3 is a graph showing the methanolysis activities of yeast MT8-1-short expressing a short-type FLO1-lipase and yeast MT8-1-long expressing a long-type FLO1-lipase.

Then, the methanolysis activities of the yeast MT8-1-short expressing the short-type FLO1-lipase, and the yeast MT8-1-long expressing the long-type FLO1-lipase were measured. To each yeast collected from a 100 ml medium in a 30 ml vial, a reaction mixture (2 ml of 0.1M phosphate buffer solution (pH 7.0), 9.65 g of soybean oil, and 0.35g of methyl alcohol) was added, and shaken at 35° C. 150 times per minute, and then the amount of produced methyl ester was measured by the method of Kaieda et al. (J. Biosci. Bioeng., 88: 627–631, 1999). The results are shown in FIG. 3.

All the types of yeast produced more methyl ester than a conventional yeast (yeast in which lipase is bound to the N-terminus of α-agglutinin and expressed on the cell surface layer (Japanese Laid-Open Patent Publication No. 11-290078)). In particular, as shown in FIG. 3, in the yeast MT8-1-short (○) expressing the short-type FLO1-lipase and the yeast MT8-1-long (Δ) expressing the long-type FLO1-lipase, the activities in producing methyl ester were very high.

Furthermore, the flocculation abilities of these strains were measured according to the method of Smit et al. (Smit et al., Appl. Environ. Microbiol., 58:3709–3714 (1992)). As a result, regarding the flocculent strains, when compared with before the plasmid was introduced, the strains expressing the long-type FLO1-lipase exhibited the flocculation ability as strong as before the transformation. However, in the strains expressing the short-type FLO1-lipase, the flocculation ability was weakened. This seems to be because the short-type FLO1-lipase has no cell wall anchoring domain, and instead the flocculation domain is embedded in the cell wall, so that the flocculation ability cannot sufficiently be exhibited.

Example 5

Construction of a Combinatorial Library of Randomly Mutated Lipase and Utilization Thereof A mutation introduction was performed with respect to the 1098 bp gene encoding the prosequence and the mature protein sequence (prolipase (ProROL)) of 366 amino acids) of Rhizopus oryzae lipase obtained in the section B of Example 1 at random by Error-prone PCR method such that a mutation of about 3 bases (introduction of a mutation of one amino acid per molecule of ProROL) was contained, and thus various mutation-introduced lipase genes were obtained. In the same manner as the section C of Example 1, mutation-introduced lipase genes obtained were inserted in the plasmid pWIFS having the 5' region of FLO1 to give a pWIFSProROL library. Each of these plasmids was introduced into the yeast YF207 strain in the same manner as in Example 3, and a combinatorial library of yeast consisting of 713 strains that displayed lipase having various mutations on the cell surface layer was produced.

A clone having transesterification activity was selected from the obtained yeast combinatorial library in the following manner. The library of 713 strains was cultivated on an SD plate (0.67% Yeast nitrogen base w/o amino acids, 0.5% glucose and 2% agar powder) for three days. Then, a soft agar SD medium (SD medium+2.5% soybean oils, 0.001% rhodamine B, 50% methanol and 0.8% agar powder) containing a fluorochrome that was kept at 45° C. after autoclaving was layered over this plate. One day later, the plate was irradiated with ultraviolet rays and the clone emitting orange fluorescence around the cell was selected to obtain clones (80 clones) that survived in the presence of methanol, which is the substrate of methanolysis.

Regarding the lipase activities of these clones, the initial rate of the transesterification by methanolysis and the hydrolysis activities by a Lipase Kit S (manufactured by DAINIPPON PHARMACEUTICAL CO., LTD.) were measured in the same manner as described in Example 4. Table 1 shows the results of those strains among these strains, in which the transesterification activities and the hydrolysis activities were changed, compared with the strain (wild-type strains) expressing lipase to which a mutation has not been introduced.

TABLE 1

| | Lipase activities | | |
|---|---|---|---|
| mutant | transesterification reaction (g/l/minute) | hydrolysis reaction (IU/ml) | transesterification/ hydrolysis |
| wild-type | 2.38 | 0.23 | 10.35 |
| S334T | 2.51 | 0.22 | 11.41 |
| P2S/F293Y | 2.04 | 0.34 | 6.00 |
| K36E | 1.85 | 0.17 | 10.88 |
| K326R | 2.24 | 0.12 | 18.67 |
| V56A/W224R | 2.01 | 0.20 | 10.05 |
| Q225H/Q294L | 0.94 | 0.14 | 6.71 |
| S10P | 1.53 | 0.17 | 9.00 |
| N62D | 1.63 | 0.20 | 8.15 |

The strain S334T had slightly higher transesterification activities than those of the wild-type strain. Furthermore, the relative values of transesterification activities with respect to the hydrolysis activities indicate that the strain P2S/F293Y exhibited a high catalytic ability specific to hydrolysis, and the strain K326R exhibited a high catalytic ability specific to transesterification. These results indicate that a mutant suitable for the purpose can be screened by preparing a combinatorial library on the yeast cell surface layer.

INDUSTRIAL APPLICABILITY

The cell surface layer-binding protein of the present invention can express a desired protein on the cell surface layer. This desired protein can be expressed so as to have sufficient activities by, depending on the position of the active center, being fused to the sugar chain-binding protein domain on its opposite side. Therefore, in particular, when expressing a protein having activities on the C-terminal portion on the cell surface layer, the present invention is very useful. Furthermore, it is possible to express more proteins efficiently by fusing the same or different proteins to both terminals of the sugar chain-binding protein domain. A combinatorial library of modified proteins is prepared on the cell surface layer, utilizing such efficient expression of proteins on the cell surface layer, so that screening can be performed easily.

The invention claimed is:

1. A yeast cell surface layer-binding protein comprising a sugar chain-binding protein domain, in which an additional protein is fused to at least an N-terminus or a C-terminus of the sugar chain-binding protein domain, wherein the sugar chain-binding protein domain includes a flocculation functional domain of a GPI anchor protein but does not include a GPI anchor attachment recognition signal sequence present in a C-terminal portion of the GPI anchor protein, wherein the GPI anchor protein is a flocculation protein of yeast.

2. The yeast cell surface layer-binding protein according to claim 1, wherein the flocculation protein is a protein selected from the group consisting of FLO1, FLO2, FLO4, FLO5, FLO9, FLO10 and FLO11.

3. The yeast cell surface layer-binding protein according to claim 1, wherein the additional protein is fused to the N-terminus of the sugar chain-binding protein domain.

4. The yeast cell surface layer-binding protein according to claim 1, wherein the additional protein is fused to the C-terminus of the sugar chain-binding protein domain.

5. The yeast cell surface layer-binding protein according to claim 1, wherein the same or different additional proteins are fused to the N-terminus and the C-terminus of the sugar chain-binding protein domain.

6. DNA encoding the yeast cell surface layer-binding protein according to claim 1.

7. A plasmid comprising the DNA according to claim 6.

8. A yeast cell wherein the DNA according to claim 6 or the plasmid according to claim 7, is introduced and the additional protein is expressed on a cell surface layer.

9. The yeast cell according to claim 8, wherein the additional protein is an enzyme.

10. A method for using the yeast cell according to claim 8, comprising contacting the additional protein with a substrate, so that the substrate is bound thereto or the substrate is converted into another substance.

11. An enzyme-containing agent comprising the yeast cell according to claim 9.

12. DNA encoding the yeast cell surface layer-binding protein according to claim 2.

13. DNA encoding the yeast cell surface layer-binding protein according to claim 3.

14. DNA encoding the yeast cell surface layer-binding protein according to claim 4.

15. DNA encoding the yeast cell surface layer-binding protein according to claim 5.

* * * * *

SEQUENCE LISTING

<160> NUMBER OF SEQ ID NOS: 5

<210> SEQ ID NO 1
<211> LENGTH: 40
<212> TYPE: DNA
<213> ORGANISM: Artificial Sequence
<220> FEATURE:
<223> OTHER INFORMATION: oligonucleotide construct

<400> SEQUENCE: 1
acatggatcc atgacaatgc ctcatcgcta tatgtttttg        40

```
<210> SEQ ID NO 2
<211> LENGTH: 40
<212> TYPE: DNA
<213> ORGANISM: Artificial Sequence
<220> FEATURE:
<223> OTHER INFORMATION: oligonucleotide construct

<400> SEQUENCE: 2
gatagatctg gtgatttgtc ctgaagatga tgatgacaaa                40

<210> SEQ ID NO 3
<211> LENGTH: 40
<212> TYPE: DNA
<213> ORGANISM: Artificial Sequence
<220> FEATURE:
<223> OTHER INFORMATION: oligonucleotide construct

<400> SEQUENCE: 3
ctccggatcc atggttcctg tttctggtaa atctggatct                40

<210> SEQ ID NO 4
<211> LENGTH: 25
<212> TYPE: DNA
<213> ORGANISM: Artificial Sequence
<220> FEATURE:
<223> OTHER INFORMATION: oligonucleotide construct

<400> SEQUENCE: 4
cgatgtcgac ttacaaacag cttcc                                25

<210> SEQ ID NO 5
<211> LENGTH: 45
<212> TYPE: DNA
<213> ORGANISM: Artificial Sequence
<220> FEATURE:
<223> OTHER INFORMATION: oligonucleotide construct

<400> SEQUENCE: 5
aatgcctcga gttaaataat tgccagcaat aaggacgcaa tgaag          45
```